(12) United States Patent
Allen et al.

(10) Patent No.: US 6,897,356 B1
(45) Date of Patent: May 24, 2005

(54) THIOREDOXIN H HOMOLOGS

(75) Inventors: Stephen M. Allen, Wilmington, DE (US); Catherine J. Thorpe, Cambridge (GB); Albert L. Lu, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/786,715

(22) PCT Filed: Sep. 7, 1999

(86) PCT No.: PCT/US99/20420

§ 371 (c)(1),
(2), (4) Date: Mar. 7, 2001

(87) PCT Pub. No.: WO00/14239

PCT Pub. Date: Mar. 16, 2000

Related U.S. Application Data

(60) Provisional application No. 60/099,501, filed on Sep. 8, 1998.

(51) Int. Cl.[7] .......................... C07H 21/04; A01H 1/00; C12N 15/29; C12N 5/14; C12P 21/02
(52) U.S. Cl. ...................... 800/278; 800/298; 435/69.1; 435/235.1; 435/252.3; 435/254.11; 435/320.1; 435/325; 435/410; 536/23.1
(58) Field of Search ................................ 800/278, 298; 536/23.1; 435/69.1, 235.1, 252.3, 257.1, 320.1, 325, 410

(56) References Cited

U.S. PATENT DOCUMENTS 5,777,200 A * 7/1998 Ryals et al. .................... 435/6

FOREIGN PATENT DOCUMENTS

| WO | 9308274 | 4/1993 |
| WO | 9519443 | 7/1995 |
| WO | 9603505 A1 | 2/1996 |
| WO | 9612799 | 5/1996 |

OTHER PUBLICATIONS

Rivera–Madrid et al., Plant Phys., vol. 102:327–328, 1993, Nucleotide sequence of a cDNA clone encoding an Arabidopsis thaliana Thioredoxin h.

Rivera–Madrid et al., PNAS, vol. 92:5620–5624, 1995, Evidence for five divergent thioredoxin h sequences in Arabidopsis thaliana.

Marty et al., Plant Mol. Biol., vol. 17:143–147, 1991, Nucleotide sequence of a cDNA encoding a tobacco thioredoxin.

EMBL Database Sequence Library Accession No: 270677, Apr. 4, 1996, Szederkenyl, J. et al., cDNA expressed in *Ricinus cotyledons*.

Brugidou et al., Mol. Gen. Genet., vol. 238:285–293, 1993, The *Nicotiana tabacum* genome encodes two cytoplasmic thioredoxin genes which are differently expressed.

Shi et al., Plant Mol. Biol., vol. 32:653–662, 1996, A novel plasma membrane–bound thioredoxin from soybean.

Buchanan et al., Arch. of Biochem. & Biophys., vol. 314(2):257–260, 1994, Thioredoxin: A multifunctional regulatory protein with a bright future in Technology and Medicine.

Gautier et al., Eur. J. Biochem., vol. 252:314–324, 1998, Characterization of wheat thioredoxin h cDNA and production of an active Triticum aestivum protein in *Escherichia coli*.

Maeda et al., Eur. J. Biochem., vol. 154:197–203, 1986, Further characterization and amino acid sequence of m–type thioredoxins from spinach chloroplasts.

EMBL Database Sequence Library Accession No: AI736736, Jun. 18, 1999, Shoemaker, R. et al., Public Soybean EST Project.

Holmgren, Ann. Rev. Biochem., vol. 54:237–271, 1985, Thioredoxin.

Holmgren, Curr. Biol., vol. 3:239–243, 1995, Thioredoxin structure and mechanism: conformational changes on oxidation of the active–site sulfhydryls to a disulfide.

Sahrawy et al., J. Mol. Evol., vol. 42:422–431, 1996, Intron position as an evolutionary marker of thioredoxins and thioredoxin domains.

NCBI Database, Accession No. P29449, Thioredoxin H–Type 1 (TRX–H1), Oct. 1, 2000.

NCBI Database, Accession No. CAA94534, thioredoxin [Ricinus communis], Apr. 4, 1996.

NCBI Database, Accession No. P29448, Thioredoxin H–Type 1(TRX–H–1), Oct. 1, 2000.

* cited by examiner

Primary Examiner—Robert A. Wax

(57) ABSTRACT

This invention relates to an isolated nucleic acid fragment encoding a thioredoxin protein. The invention also relates to the construction of a chimeric gene encoding all or a portion of the thioredoxin protein, in sense or antisense orientation, wherein expression of the chemeric gene results in production of altered levels of the thioredoxin protein in a transformed host cell.

14 Claims, No Drawings

THIOREDOXIN H HOMOLOGS

This application claims the benefit of U.S. Provisional Application No. 60/099,501, filed Sep. 8, 1998.

FIELD OF THE INVENTION

This invention is in the field of plant molecular biology. More specifically, this invention pertains to nucleic acid fragments encoding thioredoxin proteins in plants and seeds.

BACKGROUND OF THE INVENTION

Thioredoxin H is a cytosolic member of the thioredoxin family of proteins. These small proteins (typical mass of 12 kD) have been shown to play a central role in the activation of proteins by influencing the redox status of sulfhydryl groups on target proteins (Holmgren et al. (1985) *Annu. Rev. Biochem* 54:237–271; and Holmgren et al. (1995) *Structure* 3(3):239–243). Two other thioredoxin classes, F and M, are located in plastids and have been shown to be involved in redoxi mediated activation/inactivation of various photosynthetic enzymes during light/dark transitions. The cytosolic (H) form of thioredoxin has been shown to be involved in disassembly of seed storage proteins during germination and in the bread making process. In the former case storage proteins are held together in clusters by S—S bonds. On germination thioredoxin H reduces the S—S bonds and the subunits dissociate, facilitating attack by proteases. During bread making the same processes occur. Reduction of the S—S bonds causes the protein complexes to disassemble allowing them to be distributed through out the dough during mixing. During kneading the S—H bonds become oxidized and start to reassociate in a random manner, the cross linked matrix formed by this process entraps $CO_2$ formed during yeast fermentation and is responsible for the raising process. Addition of thioredoxin H to poor quality flours improves their quality for the production of bread.

Thioredoxin H has also been shown to inactivate snake and bee venom toxins and has been shown to reduce the allergenicity of cereal proteins. In the later, the process is presumably the same as described above; by reducing the S—S bonds holding the storage protein clusters together they are more susceptible to denaturation and proteolysis in the gut. Thioredoxin H may also be overexpressed in transformed corn kernels and other cereal crops. The wet milling industry, which is primarily focused on starch extraction, steeps corn in liquours of sodium metabisulphite or $SO_2$. Although this has many secondary effects (e.g., suppression of microbial activity), the primary function is to cause a dissociation of the storage proteins which leads to more efficient starch extraction. Small increases in extractable starch translate into significant increases in the profit margins for the wet millers. By overexpressing thioredoxin H in maize kernels and other cereals it may possible to improve starch recoveries, reduce steep times, and reduce or eliminate the use of sulfur compounds in the steeping process. Overexpression of thioredoxin H in maize kernels and other cereals may have the added advantage of reducing the allergenicity of any transgenic protein engineered into cereal crops with high sulfhydryl content.

SUMMARY OF THE INVENTION

The present invention relates to isolated polynucleotides comprising a nucleotide sequence encoding a first polypeptide of at least 100 amino acids that has at least 80% identity based on the Clustal Method of alignment when compared to a polypeptide selected from the group consisting of a *Momordica charantia* thioredoxin polypeptide of SEQ ID NO:2, a *Catakoa speciosa* thioredoxin polypeptide of SEQ ID NO:4, a soybean thioredoxin polypeptide of SEQ ID NO:6, a soybean thioredoxin polypeptide of SEQ ID NO:8, and a Vernonia thioredoxin polypeptide of SEQ ID NO:10. The present invention also relates to an isolated polynucleotide comprising the complement of the nucleotide sequences described above. It is preferred that the isolated polynucleotides of the claimed invention consists of regions of the isolated polynucleotide selected from the group SEQ ID NO:1, 3, 5, 7 and 9 that codes for the polypeptide selected from the group consisting of SEQ ID NO:2, 4, 6, 8 and 10. The present invention also relates to an isolated polynucleotide comprising a nucleotide sequences of at least one of 40 (preferably 30) contiguous nucleotides derived from a nucleotide sequence selected from the group consisting of SEQ ID NO:1, 3, 5, 7, 9 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eucaryotic, such as a yeast or a plant cell, or procaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene or isolated polynucleotide of the present invention, the process comprising either transforming or transfecting an isolated compatible host cell with a chimeric gene or isolated polynucleotide of the present invention.

The present invention relates to a thioredoxin polypeptide of at least 100 amino acids comprising at least 80% homology based on the Clustal method of alignment compared to a polypeptide selected from the group consisting of SEQ ID NO:2, 4, 6, 8 and 10.

The present invention relates to a method of selecting an isolated polynucleotide that affects the level of expression of a thioredoxin polypeptide in a plant cell, the method comprising the steps of:

constructing an isolated polynucleotide or chimeric gene of the present invention;
introducing the isolated polynucleotide into a plant cell;
measuring the level of thioredoxin polypeptide in the plant cell containing the polynucleotide; and
comparing the level of thioredoxin polypeptide in the plant cell containing the isolated polynucleotide with the level of thioredoxin polypeptide in a plant cell that does not contain the isolated polynucleotide.

The present invention relates to a method of obtaining a nucleic acid fragment encoding a substantial portion of a thioredoxin gene, preferably a plant thioredoxin gene, comprising the steps of: synthesizing an oligonucleotide primer comprising a nucleotide sequence of at least one of 40 (preferably 30) contiguous nucleotides derived from a nucleotide sequence selected from the group consisting of SEQ ID NO:1, 3, 5, 7, 9 and the complement of such nucleotide sequences; and amplifying a nucleic acid fragment (preferably a cDNA inserted in a cloning vector) using the oligonucleotide primer. The amplified nucleic acid fragment preferably well encode a portion of a thioredoxin polypeptide amino acid sequence.

The present invention also relates to a method of obtaining a nucleic acid fragment encoding all or a substantial portion of the amino acid sequence encoding a thioredoxin protein comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

BRIEF DESCRIPTION OF THE SEQUENCE DESCRIPTIONS

The invention can be more fully understood from the following detailed description and the accompanying Sequence Listing which form a part of this application.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. The sequence descriptions and Sequence Listing attached hereto comply with the rules governing nucleotide and/or amino acid sequence disclosures in patent applications as set forth in 37 C.F.R. §1.821–1.825.

TABLE 1

Thioredoxin Proteins

| | | SEQ ID NO: | |
|---|---|---|---|
| Protein | Clone Designation | (Nucleotide) | (Amino Acid) |
| Thioredoxin H | fds.pk0001.e9 | 1 | 2 |
| Thioredoxin H | ncs.pk0010.e3 | 3 | 4 |
| Thioredoxin H | sah1c.pk001.l17 | 5 | 6 |
| Thoredoxin H | sfl1.pk0029.e2 | 7 | 8 |
| Thoredoxin H | vs1n.pk0012.f3 | 9 | 10 |

The Sequence Listing contains the one letter code for nucleotide sequence characters and the three letter codes for amino acids which is in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as nucleic acid fragment. A polynucleotide may be a polymer of RNA or DNA is single- or double-stranded, that optionally contains synthetic, non-natural or altered nucleotide bases. A polynucleotide in the form of a polymer of DNA may be comprised of one or more segments of cDNA, genomic DNA, or synthetic DNA.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, a polynucleotide comprising a nucleotide sequence of at least one of 40 (preferably 30) contiguous nucleotides derived from a nucleotide sequence selected from the group consisting of SEQ ID NO:1, 3, 5, 7, 9 and the complement of such nucleotide sequences may be used in methods of selecting an isolated polynucleotide that affects the expression of a thioredoxin polypeptide in a plant cell.

Moreover, substantially similar nucleic acid fragments may also be characterized by their ability to hybridize. Estimates of such homology are provided by either DNA—DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments; such as genes that duplicate functional enzymes from closely related organisms. Post-hybridization washes determine stringency conditions. One set of preferred conditions uses a series of washes starting with 6× SSC, 0.5% SDS at room temperature for 15 min, then repeated with 2× SSC, 0.5% SDS at 45° C. for 30 min, and then repeated twice with 0.2× SSC, 0.5% SDS at 50° C. for 30 min. A more preferred set of stringent conditions uses higher temperatures in which the washes are identical to those above except for the temperature of the final two 30 min washes in 0.2× SSC, 0.5% SDS was increased in 60° C. Another preferred set of highly stringent conditions uses two final washes in 0.1× SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (polynucleotides) encode amino acid sequences that are 80% identical to the amino acid sequences reported herein. Preferred nucleic acid fragment encode amino acid sequences that are 85% identical to the amino acid sequences reported herein. More preferred nucleic acid fragments encode amino acid sequences that are 90% identical to the amino acid sequences reported herein. Most preferred are nucleic acid fragments that encode amino acid sequences that are 95% identical to the amino acid sequences reported herein. Sequence alignments and percent identity calculations were performed using the Megalign program of the LASERGENE bioinformatics computing suite (DNASTAR Inc., Madison, Wis.). Multiple alignment of the sequences was performed using the Custodial method of alignment (Higgins and Sharp (1989) *CABIOS*. 5:151–153) with the default parameters (GAP PENALTY= 10, GAP LENGTH PENALTY=10). Default parameter for pairwise alignments using the Clustal method were KTUPLE1, GAP PENALTY=3, WINDOW=5, AND DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequence can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that is frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased toward those condons favored by the host. Determination of preferred condons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complimentary of an antisense RNA may be with any part of the specific nucleotide sequence, i.e., at the 5' non-coding sequence, 3' non-coding sequence, introns or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts of proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature (London)* 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual;* Cold Spring Harbor Laboratory Press: Cold Spring Harbor, 1989 (hereinafter "Maniatis").

Nucleic acid fragments encoding at least a portion of several thioredoxin proteins have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other thioredoxin H proteins, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designated and synthesized by methods known in the art (Maniatis). Moreover, the entire sequences can be used directly to synthesize DNA probes by methods known to the skilled artisan such as random primer DNA labeling; nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 40 (preferably 30) contiguous nucleotides derived from a nucleotide sequence selected from the group consisting of SEQ ID NO:1, 3, 5, 7, 9 and the complement of such nucleotide sequences may be used in such methods to obtain a nucleic acid fragment encoding a substantial portion of an amino acid sequence of a thioredoxin polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34 Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of thioredoxin activity in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3'Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J.* 4:2411–2418; De Almeida et al. (1989) *Mol. Gen. Genetics* 218:78–86), and thus the multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applicants it may be useful to direct the instant polypeptides to different cellular compartments, or to facilitate its secretion from the cell. It is thus envisioned that the chimeric gene described above may be further supplemented by alternating the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. No. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. addition, the ability to restrict the expression of specific phenotype to the reproductive tissues of the plant by the use of tissue specific promoters may confer argonomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenic for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded thioredoxin protein. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individual representing parent and progeny of a defined genetic cross. Segregation of the DNA polymorphisms is noted and used to calculate the position of the instant nucleic acid sequence in the genetic map previously obtained using this population (Botstein et al. (1980) *Am. J. Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask) (1991) *Trends Genet.* 7:149–154). Although current methods of FISH mapping favor use of large clones (several to several hundred KB; see Laan et al. (1995) *Genome Res.* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific multiplication (Kazazian (1989) *J. Lab. Clin. Med.* 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res.* 18:3671), Radiation Hybrid Mapping (Walter et al. (1997) *Nat. Genet.* 7:22–28) and Happy Mapping (Dear and Cook (1989) *Nucleic Acid Res.* 17:6795–6807). For these methods, the sequence of a nucleic acid fragment is used to design and produce printer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide.

Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptides can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various barley, Catalpa, pear, soybean and Vernonia tissues were prepared. The characteristics of the libraries are described below.

TABLE 2 cDNA Libraries from Barley, Catalpa, Pear, Soybean and Vernonia

| Library | Tissue | Clone |
|---|---|---|
| fds | *Momordica charantia* developing seed | fds.pk0001.e9 |
| ncs | Catalpa speciosa developing Seed | ncs.pk0010.e3 |
| sah1c | Soybean sprayed with Authority herbicide. | sah1c.pk001.l17 |
| sfl1 | Soybean immature flower | sfl1.pk0029.e2 |
| vs1n | Vernonia Seed* | vs1n.pk0012.f3 |

*This library was normalized essentially as described in U.S. Pat. No. 5,482,845, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequence.

Example 2

Identification of cDNA Clones cDNA clones encoding thioredoxin proteins were identified by conducting BLAST (Basic Local Alignment Search Tool; Altschul et al. (1993) *J. Mol. Biol.* 215:403–410 searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Natl. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Thioredoxin H

The BLASTX search using the EST sequences from clones listed in Table 3 revealed similarity of the polypeptide encoded by the cDNAs to thioredoxin H from *Arabidopsis thaliana* (NCBI Identifier No. gi 267122), *Nicotiana tabacum* (NCBI Identifier No. gi 267124) and *Ricinus communis* (NCBI Identifier No. gi 1255954). Shown in Table 3 are the BLAST results for individual ESTs ("EST"), the sequences of the entire cDNA inserts comprising the indicated cDNA clones ("FIS"), or contigs assembled from two or more ESTs ("Contig"):

TABLE 3

BLAST Results for Sequences Encoding Polypeptides Homologous to *Arabidopsis thaliana*, *Nicotiana tabacum* and *Ricinus communis* Thioredoxin H

| Clone | Status | BLAST pLog Score |
|---|---|---|
| fds.pk0001.e9 | FIS | 35.50 (gi 267122) |
| ncs.pk0010.e3 | FIS | 48.40 (gi 267124) |
| sah1c.pk001.l17 | FIS | 49.00 (gi 1255954) |
| sfl1.pk0029.e2 | FIS | 41.00 (gi 1255954) |
| vs1n.pk0012.f3 | FIS | 41.70 (gi 267124) |

The data in Table 4 represents a calculation of the percent identity of the amino acid sequences set forth in SEQ ID NOs:2, 4, 6, 8 and 10 and the *Arabidopsis thaliana*, *Nicotiana tabacum* and *Ricinus communis* sequences (SEQ ID NOs.:11, 12 and 13 respectively). The percent identity between the amino acid sequences set forth in SEQ ID NOs:2, 4, 6, 8 and 10 ranged from 49% to 80%.

TABLE 4

Percent Identity of Amino Acid Sequences Deduced From the Nucleotide Sequences of cDNA Clones Encoding Polypeptides Homologous to *Arabidopsis thaliana*, *Nicotiana tabacum* and *Ricinus communis* Thioredoxin H

| SEQ ID NO. | Percent Identity to |
| --- | --- |
| 2 | 62% (gi 267122) |
| 4 | 75% (gi 267124) |
| 6 | 75% (gi 1255954) |
| 8 | 65% (gi 1255954) |
| 10 | 69% (gi 267124) |

Sequence alignments and percent identity calculations were performed using the Megalign program of the LASERGENE bioinformatics computing suite (DNASTAR Inc., Madison, Wis.). Multiple alignment of the sequences were performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5. Sequence alignment and BLAST scores and probabilities indicate that the nucleic acid fragments comprising the instant cDNA clones encode a substantial portion of a thioredoxin H. These sequences represent the first Catalpa pear, soybean and Vernonia sequences encoding thioredoxin H.

Example 4

Expression of Chimeric Genes in Monocot Cells

A chimeric gene comprising a cDNA encoding the instant polypeptides in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI SmaI) can be incorporated into the oligonucleotides to provide proper orientation of the DNA fragment when inserted into the digest vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptides, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules, Calif.), using a helium pressure of 1000 psi, a gap distance of 0.5 cm and a flying distance of 1.0 cm.

For bombardment, the embryogenic tissue is placed on filter paper over agarose-solidifed N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium.

These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) Bio/Technology 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptide in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), SmaI, KpnI and XbaI. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embroys may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1978) *Nature* (London) 327:70–73, U.S. Pat. No. 4,945,050). A DuPont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli;* Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptides and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the issue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligand adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the instant polypeptides are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

What is claimed is:

1. An isolated polynucleotide comprising:
   (a) a nucleotide sequence encoding a polypeptide having thioredoxin h activity, wherein the polypeptide has an amino acid sequence of at least 80% sequence identity, based on the Clustal V method of alignment, when compared to SEQ ID NO:6, or
   (b) a full-length complement of the nucleotide sequence of (a).

2. The polynucleotide of claim 1, wherein the amino acid sequence of the polypeptide has at least 85% sequence identity, based on the Clustal V method of alignment, when compared to SEQ ID NO:6.

3. The polynucleotide of claim 1, wherein the amino acid sequence of the polypeptide has at least 90% sequence identity, based on the Clustal V method of alignment, when compared to SEQ ID NO:6.

4. The polynucleotide of claim 1, wherein the amino acid sequence of the polypeptide has at least 95% sequence identity, based on the Clustal V method of alignment, when compared to SEQ ID NO:6.

5. The polynucleotide of claim 1, wherein the amino acid sequence of the polypeptide comprises SEQ ID NO:6.

6. The polynucleotide of claim 1 wherein the nucleotide sequence comprises SEQ ID NO:5.

7. A vector comprising the polynucleotide of claim 1.

8. A recombinant DNA construct comprising the polynucleotide of claim 1 operably linked to at least one regulatory sequence.

9. A method for transforming a cell, comprising transforming a cell with the polynucleotide of claim 1.

10. A cell comprising the recombinant DNA construct of claim 8.

11. A method for producing a plant comprising transforming a plant cell with the polynucleotide of claim 1 and regenerating a plant from the transformed plant cell.

12. A plant comprising the recombinant DNA construct of claim 8.

13. A seed comprising the recombinant DNA construct of claim 8.

14. A virus comprising the recombinant DNA construct of claim 8.

* * * * *

UNITED STATES PATENT AND TRADEMARK OFFICE
CERTIFICATE OF CORRECTION

PATENT NO. : 6,897,356 B1  Page 1 of 1
DATED : May 24, 2005
INVENTOR(S) : Allen et al.

It is certified that error appears in the above-identified patent and that said Letters Patent is hereby corrected as shown below:

<u>Title page,</u>
Item [75] Inventors, delete "Catherine J. Thorpe, Cambridge (GB); Albert L. Lu, Newark, DE (US)" and insert -- John D. Everard, Wilmington, DE (US) --.

Signed and Sealed this

Eleventh Day of April, 2006

JON W. DUDAS
*Director of the United States Patent and Trademark Office*

SEQUENCE LISTING

<160> NUMBER OF SEQ ID NOS: 13

<210> SEQ ID NO 1
<211> LENGTH: 870
<212> TYPE: DNA
<213> ORGANISM: Momordica charantia

<400> SEQUENCE: 1

```
gcacgagggg gaagactttt tgcaggactg cgatttctgt ttacatcaat ggctgaagaa      60
gggcaagtga ttgcgtgtca taagatagat gaatgggagg gacaattagg aaaatggaag     120
gattctgaga aactggttgt ggtggatttt actgcttcct ggtgcgggcc atgccgggca     180
attgctccat atttcacaga attggctaag aataacccaa atgtcgcttt cctgaaagtc     240
gacgttgacg aattgaacag tgttgctagc aagtgggaga ttaatgcaat gccaacgttt     300
gttttcctga aaaagggaa aataattgag aagatcgttg gtgctgataa agtggggctg     360
tcgaagaaaa tattagagct tagtggaact actcccgctg ctacttctac tgcttagaca     420
gtctgcttgg aggatgtgat ccctctggtg caatggtgat tccgctttgg agtttgatct     480
aattgtggat gaaactgtgt ctaaaagatg ttaattgttt ggccttttgg gttttcccct     540
ttttaagttt ggatcatgtg cgcacctctc agttgtgatt ctggtgctag aagcttcagg     600
tttcaatgtg gaataaatgg gggcacctgc tctgaaattg aatgacattt ttgcacactt     660
ttcattattc ttctgtaaga acttgaattc actgtttttt tttaatctaa ttcttcgtag     720
cagtacagtg agatgttctt tcagcttgtt tagcaacttc ttaatccctc tcctggcttt     780
tattttctta ttattggaat ggaacttaga agaatcgaag ttgttatgat ttgttaaaag     840
tatttgttgt taaaaaaaaa aaaaaaaaa                                       870
```

<210> SEQ ID NO 2
<211> LENGTH: 122
<212> TYPE: PRT
<213> ORGANISM: Momordica charantia

<400> SEQUENCE: 2

```
Met Ala Glu Glu Gly Gln Val Ile Ala Cys His Lys Ile Asp Glu Trp
 1               5                  10                  15

Glu Gly Gln Leu Gly Lys Trp Lys Asp Ser Glu Lys Leu Val Val Val
            20                  25                  30
```

Asp Phe Thr Ala Ser Trp Cys Gly Pro Cys Arg Ala Ile Ala Pro Tyr
         35                  40                  45

Phe Thr Glu Leu Ala Lys Asn Asn Pro Asn Val Ala Phe Leu Lys Val
     50                  55                  60

Asp Val Asp Glu Leu Asn Ser Val Ala Ser Lys Trp Glu Ile Asn Ala
 65                  70                  75                  80

Met Pro Thr Phe Val Phe Leu Lys Lys Gly Lys Ile Ile Glu Lys Ile
                 85                  90                  95

Val Gly Ala Asp Lys Val Gly Leu Ser Lys Lys Ile Leu Glu Leu Ser
             100                 105                 110

Gly Thr Thr Pro Ala Ala Thr Ser Thr Ala
             115                 120

<210> SEQ ID NO 3
<211> LENGTH: 574
<212> TYPE: DNA
<213> ORGANISM: Catalpa speciosa

<400> SEQUENCE: 3
gcacgagggc ataaatacct tgtaattggg gattttttcgg agtaaaaaag ggaaatcgga     60
aaatggcttc ttcagaagag ggacaagtga tcggttgcca ctccgtcgac gagtggaagg    120
agcagttcca gaagggtgtt gactctaaga aactggtggt aatagacttc acggcttcct    180
ggtgcggacc atgccgtttc attgctccaa tcttggctga gatggccaag aagacacccc    240
atgtcatatt cctgaaagtc gacgtggatg aactcaagac tgttgctgag gaattcaaag    300
tggaggctat gccgaccttc gtgttcctca aggaagggaa agaagtggaa aggcttgtgg    360
gagcaaggaa ggaggaattg caggccacag ttgagaaaca tggcgctatc actgcttgat    420
gctgtttcaa tgtttagtta tgtaatatat gatgatgctt ggaataataa tgtcttaagt    480
tatccagatc gtatgtgact gacgtttctg ttgttatgtg gattgttatt gttaatgtaa    540
tgtaatggag tgtcttaaaa aaaaaaaaaa aaaa                                574

<210> SEQ ID NO 4
<211> LENGTH: 118
<212> TYPE: PRT
<213> ORGANISM: Catalpa speciosa

<400> SEQUENCE: 4

Met Ala Ser Ser Glu Glu Gly Gln Val Ile Gly Cys His Ser Val Asp
 1               5                  10                  15

Glu Trp Lys Glu Gln Phe Gln Lys Gly Val Asp Ser Lys Lys Leu Val
             20                  25                  30

Val Ile Asp Phe Thr Ala Ser Trp Cys Gly Pro Cys Arg Phe Ile Ala
         35                  40                  45

Pro Ile Leu Ala Glu Met Ala Lys Lys Thr Pro His Val Ile Phe Leu
     50                  55                  60

Lys Val Asp Val Asp Glu Leu Lys Thr Val Ala Glu Glu Phe Lys Val
 65                  70                  75                  80

Glu Ala Met Pro Thr Phe Val Phe Leu Lys Gly Lys Glu Val Glu
                 85                  90                  95

Arg Leu Val Gly Ala Arg Lys Glu Glu Leu Gln Ala Thr Val Glu Lys
             100                 105                 110

His Gly Ala Ile Thr Ala
         115

<210> SEQ ID NO 5
<211> LENGTH: 738
<212> TYPE: DNA
<213> ORGANISM: Glycine max

<400> SEQUENCE: 5

| | | | | | |
|---|---|---|---|---|---|
| gcaccaggaa | attctttagt | tgtaactgac | aaagttttct | gagaaaataa | ggattattat | 60 |
| tgagagaatg | gctggctcat | cggaagaggg | acaagtcatt | agctgccaca | ccgttgaaga | 120 |
| atggaacgat | caactccaga | agggcaacga | atccaagaaa | ctcattgttg | tggattttac | 180 |
| tgcttcttgg | tgtggaccat | gccgtttcat | tgcaccattc | ttggctgagc | tggctaagaa | 240 |
| gttcacaagt | gtcatattcc | taaaggtgga | tgtggacgaa | ttaaagagtg | tttctcaaga | 300 |
| ttgggctatt | gaggctatgc | ccacttttgt | gtttgtgaaa | gagggaacgc | ttctggacaa | 360 |
| agtggtggga | gcaaagaagg | atgagctgca | gcagaaaata | cagaaacatg | tggcttcagc | 420 |
| tagtgcttaa | tctagctcac | cttcagaaac | tttatatatg | cgctttcttt | tcataatctt | 480 |
| gtactagact | tatgttggta | tttctgttat | tgcaccaatc | agcttttcaa | aggtgatgac | 540 |
| tcctatcatc | tatttctgaa | tagtagtaac | tggtcctttc | ttccgtctta | aataatagtg | 600 |
| gatggtgcta | tatcatgaat | cttaattaca | tagaccttcc | tgttttccct | tttagtatta | 660 |
| aaaaaaaaaa | aaaaaaaaaa | aaaaaaaaaa | aaaaaaaaaa | aaaaaaaaaa | aaacaataaa | 720 |
| aaaaacaaaa | aaaaaaaa | | | | | 738 |

<210> SEQ ID NO 6
<211> LENGTH: 120
<212> TYPE: PRT
<213> ORGANISM: Glycine max

<400> SEQUENCE: 6

Met Ala Gly Ser Ser Glu Glu Gly Gln Val Ile Ser Cys His Thr Val
 1               5                  10                  15

Glu Glu Trp Asn Asp Gln Leu Gln Lys Gly Asn Glu Ser Lys Lys Leu
            20                  25                  30

Ile Val Val Asp Phe Thr Ala Ser Trp Cys Gly Pro Cys Arg Phe Ile
        35                  40                  45

Ala Pro Phe Leu Ala Glu Leu Ala Lys Lys Phe Thr Ser Val Ile Phe
    50                  55                  60

Leu Lys Val Asp Val Asp Glu Leu Lys Ser Val Ser Gln Asp Trp Ala
65                  70                  75                  80

Ile Glu Ala Met Pro Thr Phe Val Phe Val Lys Glu Gly Thr Leu Leu
                85                  90                  95

Asp Lys Val Val Gly Ala Lys Lys Asp Glu Leu Gln Gln Lys Ile Gln
            100                 105                 110

Lys His Val Ala Ser Ala Ser Ala
        115                 120

<210> SEQ ID NO 7
<211> LENGTH: 601
<212> TYPE: DNA
<213> ORGANISM: Glycine max

<400> SEQUENCE: 7

| | | | | | |
|---|---|---|---|---|---|
| gcacgagctc | tctctctcta | gacttagatt | ttgtgaatgg | ctgaagtgga | agagggacag | 60 |
| gtcatcggcg | tccacaccgt | tgatgagtgg | aagctgcaac | tccagaatgc | aaaagactcc | 120 |
| aaaaaactga | ttgtggtgga | ttttactgct | tcctggtgtg | gtccatgccg | ttttatggcc | 180 |

-continued

```
ccagttcttg cagagattgc aaagaaaact cctgaattga tcttcctcaa agtggatgtg    240
gatgaagtga ggcctgttgc tgaggaatat tccattgagg ccatgccaac cttcctcttc    300
ttgaaagatg gcgagatcgt ggacaaggtg gttggtgcta gtaaggatga ccttcaagcc    360
accatagcca agcatgcatc tgctgttgct gctgcttctt cttcttgaag tgaagtatca    420
taatatgaaa gaagacaaag aataatgcat tttaatgttt tcaagtcagt ttggatgttt    480
tctctatgga cattgagttg gcagaacatc gagtgatgta taaaaataaa attgttgcat    540
tgtctttttt tcgtaaaaaa aaaaaaaaaa aaaaaaaaaa aaaaaaaaaa aaaaaaaaaa    600
a                                                                    601
```

<210> SEQ ID NO 8
<211> LENGTH: 123
<212> TYPE: PRT
<213> ORGANISM: Glycine max

<400> SEQUENCE: 8

```
Met Ala Glu Val Glu Glu Gly Gln Val Ile Gly Val His Thr Val Asp
  1               5                  10                  15

Glu Trp Lys Leu Gln Leu Gln Asn Ala Lys Asp Ser Lys Lys Leu Ile
             20                  25                  30

Val Val Asp Phe Thr Ala Ser Trp Cys Gly Pro Cys Arg Phe Met Ala
         35                  40                  45

Pro Val Leu Ala Glu Ile Ala Lys Lys Thr Pro Glu Leu Ile Phe Leu
     50                  55                  60

Lys Val Asp Val Asp Glu Val Arg Pro Val Ala Glu Glu Tyr Ser Ile
 65                  70                  75                  80

Glu Ala Met Pro Thr Phe Leu Phe Leu Lys Asp Gly Glu Ile Val Asp
                 85                  90                  95

Lys Val Val Gly Ala Ser Lys Asp Asp Leu Gln Ala Thr Ile Ala Lys
            100                 105                 110

His Ala Ser Ala Val Ala Ala Ala Ser Ser Ser
        115                 120
```

<210> SEQ ID NO 9
<211> LENGTH: 614
<212> TYPE: DNA
<213> ORGANISM: Vernonia mespilifolia

<400> SEQUENCE: 9

```
gcacgaggct aaataccatt tgaaagctaa aaaaaaatct ttgaattagg ttttcttgaa     60
gaagtttgag aaaaaaaatg gcggaagaag gagttgtaac cggaatccac accgtcgacc    120
agtggaatga gcaacttgag aagcacaagg gaactgacaa attggtggtt gtggatttca    180
ccgcctcatg gtgtggtcct tgccgtgtga ttgcaccaat cttggctgat tttgctaaga    240
agatgcccca tgttaccttc cttaaggttg atgtggatga actcgagagc gttgctcagg    300
agtggtcagt ggaggcaatg ccgactttcc tgtttctcaa gggcggagtg aaagtggaca    360
aggttgtggg tgctaagaaa gacgaacttc atgcctgcat cgtcaagcat tctgctgcta    420
cagtttctgc ttaacgtact acataatatg attatcttat cagcaactta ttagtctctt    480
ttcggatgtg ttgttgattt gctttgtggt aaaaccttag attttgaata ttgtccttgt    540
aaccttgggt tataacttgc tctttcatct atatgcataa attgaagttg ctgtattaaa    600
aaaaaaaaaa aaaa                                                      614

```
<210> SEQ ID NO 10
<211> LENGTH: 118
<212> TYPE: PRT
<213> ORGANISM: Vernonia mespilifolia

<400> SE

```
                            -continued

Cys Arg Phe Ile Ala Pro Ile Leu Ala Asp Ile Ala Lys Lys Met Pro
    50                  55                  60

His Val Ile Phe Leu Lys Val Asp Val Asp Glu Leu Lys Thr Val Ser
 65              70                  75                      80

Ala Glu Trp Ser Val Glu Ala Met Pro Thr Phe Val Phe Ile Lys Asp
            85                  90                  95

Gly Lys Glu Val Asp Arg Val Val Gly Ala Lys Lys Glu Glu Leu Gln
           100                 105                 110

Gln Thr Ile Val Lys His Ala Ala Pro Ala Thr Val Thr Ala
           115                 120                 125

<210> SEQ ID NO 13
<211> LENGTH: 118
<212> TYPE: PRT
<213> ORGANISM: Ricinus communis

<400> SEQUENCE: 13

Met Ala Ala Glu Glu Gly Gln Val Ile Gly Cys His Thr Val Glu Ala
  1               5                  10                  15

Trp Asn Glu Gln Leu Gln Lys Gly Asn Asp Thr Lys Gly Leu Ile Val
             20                  25                  30

Val Asp Phe Thr Ala Ser Trp Cys Gly Pro Cys Arg Phe Ile Ala Pro
            35                  40                  45

Phe Leu Ala Glu Leu Ala Lys Lys Leu Pro Asn Val Thr Phe Leu Lys
    50                  55                  60

Val Asp Val Asp Glu Leu Lys Thr Val Ala His Glu Trp Ala Val Glu
 65              70                  75                      80

Ser Met Pro Thr Phe Met Phe Leu Lys Glu Gly Lys Ile Met Asp Lys
            85                  90                  95

Val Val Gly Ala Lys Lys Asp Glu Leu Gln Gln Thr Ile Ala Lys His
           100                 105                 110

Met Ala Thr Ala Ser Thr
           115
```